(12) United States Patent
Bellows

(10) Patent No.: US 10,874,477 B2
(45) Date of Patent: Dec. 29, 2020

(54) MODULAR ADAPTERS FOR MEDICAL DEVICE SUPPORT SYSTEM

(71) Applicant: American Sterilizer Company, Mentor, OH (US)

(72) Inventor: Lance Clark Bellows, Painesville, OH (US)

(73) Assignee: American Sterilizer Company, Mentor, OH (US)

( * ) Notice: Subject to any disclaimer, the term of this patent is extended or adjusted under 35 U.S.C. 154(b) by 0 days.

(21) Appl. No.: 16/702,903

(22) Filed: Dec. 4, 2019

(65) Prior Publication Data

US 2020/0246108 A1 Aug. 6, 2020

Related U.S. Application Data

(60) Provisional application No. 62/799,096, filed on Jan. 31, 2019, provisional application No. 62/799,100, (Continued)

(51) Int. Cl.
*F16M 13/02* (2006.01)
*A61B 90/50* (2016.01)
*A61B 34/00* (2016.01)

(52) U.S. Cl.
CPC .............. *A61B 90/50* (2016.02); *A61B 34/71* (2016.02); *F16M 13/022* (2013.01); (Continued)

(58) Field of Classification Search
CPC . A61G 12/004; F16M 2200/066; A61B 90/50
See application file for complete search history.

(56) References Cited

U.S. PATENT DOCUMENTS 4,673,154 A * 6/1987 Karapita ............. A61M 5/1415
248/320
5,490,652 A * 2/1996 Martin ................. A61B 6/4464
248/282.1
(Continued)

FOREIGN PATENT DOCUMENTS

EP 3009728 A1 4/2016
WO 200145627 A1 6/2001
(Continued)

OTHER PUBLICATIONS

International Search Report and Written Opinion for corresponding International Application PCT/US2019/064386 dated Mar. 26, 2020.

*Primary Examiner* — Bradley Duckworth
(74) *Attorney, Agent, or Firm* — Renner, Otto, Boisselle & Sklar, LLP

(57) ABSTRACT

A medical device support system adapter for connection to a load balancing arm of a medical device support system. The adapter includes a body having a central axis, a connection component at one end of the body and an interface at an opposite end of the body. The body is rotatably connectable to another component of the medical device support system. The interface is connectable to a hub of the load balancing arm of the medical device support system. The interface has at least two mounting bolt holes equally angularly spaced apart about the central axis such that the body is connectable to the hub of the load balancing arm in at least two different angular positions of the body about the central axis.

27 Claims, 11 Drawing Sheets

Related U.S. Application Data filed on Jan. 31, 2019, provisional application No. 62/799,113, filed on Jan. 31, 2019, provisional application No. 62/799,202, filed on Jan. 31, 2019.

(52) U.S. Cl.
CPC ... *A61B 2034/715* (2016.02); *A61B 2090/506* (2016.02); *A61B 2090/508* (2016.02); *A61B 2090/5025* (2016.02); *F16M 2200/022* (2013.01); *F16M 2200/041* (2013.01); *F16M 2200/066* (2013.01)

(56) References Cited

U.S. PATENT DOCUMENTS

| | | | | |
|---|---|---|---|---|
| 5,704,100 A * | 1/1998 | Swan | ............ | F16B 21/186 24/546 |
| 6,095,468 A * | 8/2000 | Chirico | ............ | F16M 11/2014 248/125.7 |
| 6,471,363 B1 * | 10/2002 | Howell | ............ | E04B 9/006 348/370 |
| 6,817,585 B2 * | 11/2004 | Wagner | ............ | F16M 11/10 248/324 |
| 7,097,145 B2 * | 8/2006 | Turner | ............ | F16M 11/10 248/274.1 |
| 7,770,860 B1 * | 8/2010 | Culpepper | ............ | A61G 12/002 248/324 |
| 8,424,833 B2 * | 4/2013 | Muller | ............ | F16M 11/08 248/324 |
| 9,528,536 B2 * | 12/2016 | Bally | ............ | F16M 13/022 |
| 9,999,480 B2 * | 6/2018 | Oginski | ............ | A61G 12/002 |
| 2003/0141426 A1 * | 7/2003 | Wagner | ............ | F16M 13/02 248/324 |
| 2004/0262484 A1 * | 12/2004 | Wagner | ............ | F16M 11/2064 248/324 |
| 2006/0102811 A1 * | 5/2006 | Musset | ............ | F16M 11/24 248/121 |
| 2007/0126318 A1 * | 6/2007 | Hamberg | ............ | A61G 12/004 312/209 |
| 2010/0074681 A1 * | 3/2010 | Jamalzadeh | ............ | F16M 13/02 403/327 |
| 2016/0091117 A1 * | 3/2016 | Boccoleri | ............ | F16M 11/2014 348/804 |
| 2017/0290725 A1 | 10/2017 | Oginski et al. | | |
| 2017/0304022 A1 | 10/2017 | Oginski et al. | | |
| 2018/0228680 A1 * | 8/2018 | Oginski | ............ | A61B 90/50 |
| 2020/0069381 A1 * | 3/2020 | Betsugi | ............ | A61B 34/35 |
| 2020/0069385 A1 * | 3/2020 | Ago | ............ | A61B 90/50 |
| 2020/0129052 A1 * | 4/2020 | Unai | ............ | A61B 90/50 |

FOREIGN PATENT DOCUMENTS

| | | |
|---|---|---|
| WO | 2003040609 A1 | 5/2003 |
| WO | 2016058707 A2 | 4/2016 |

* cited by examiner

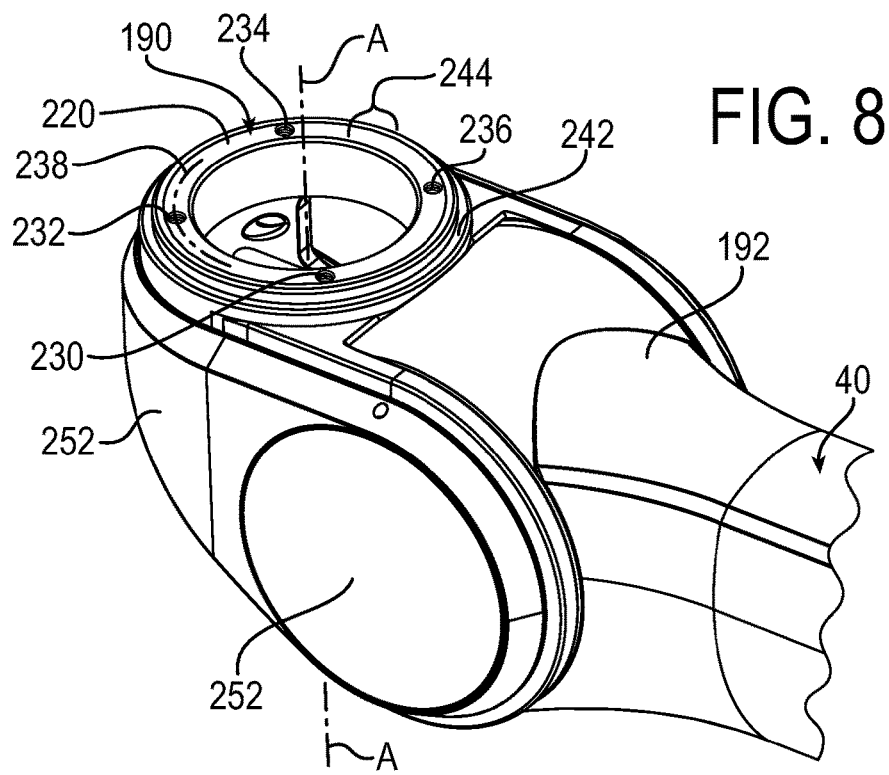
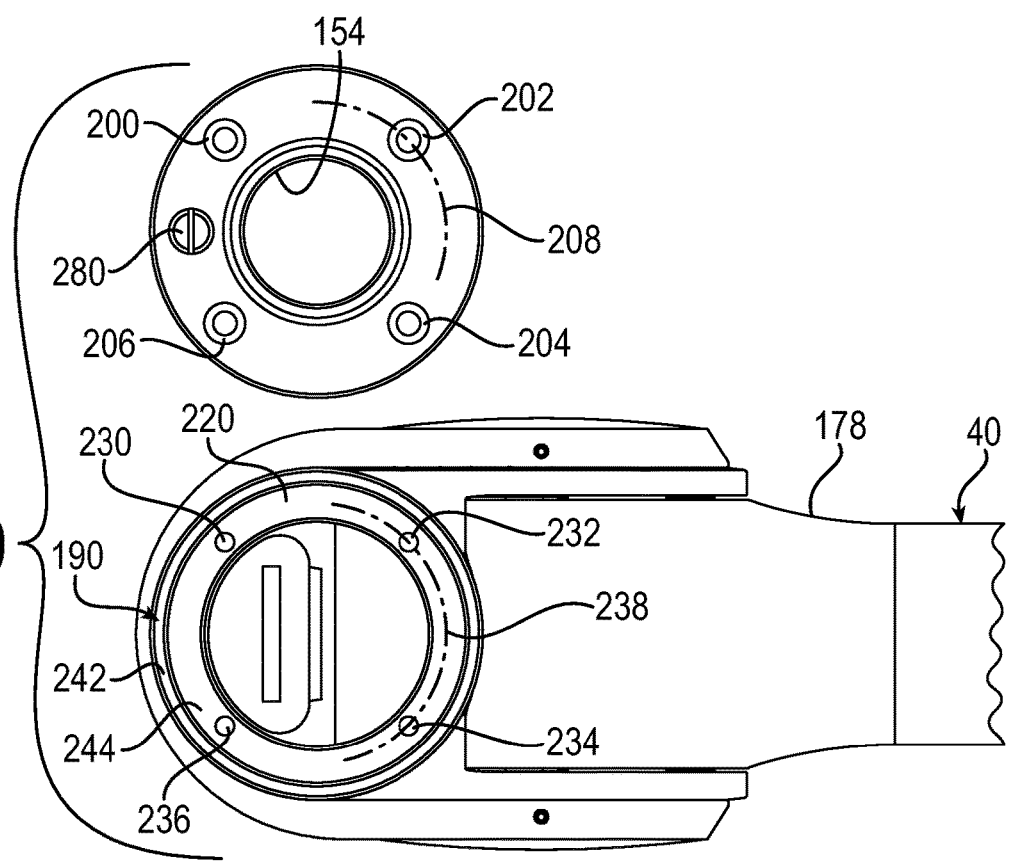

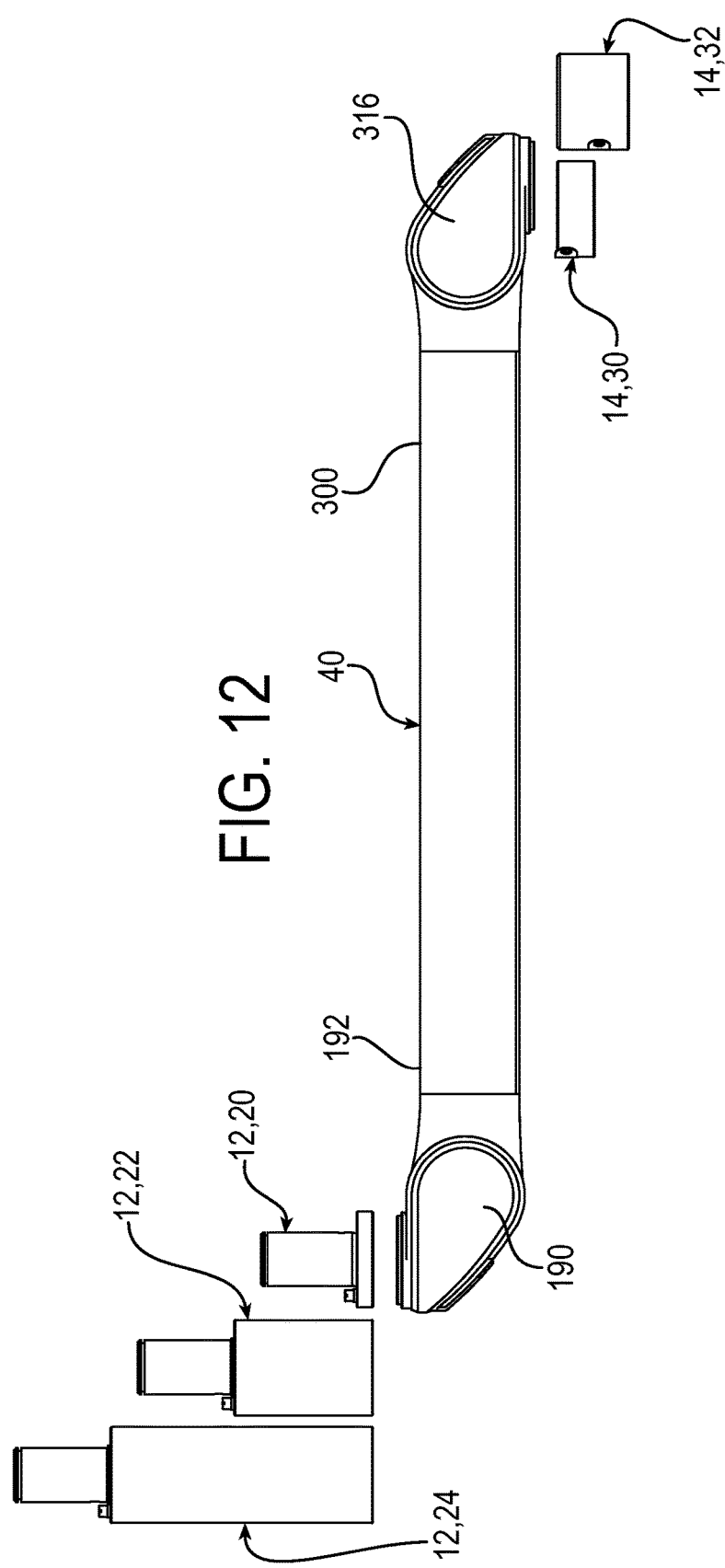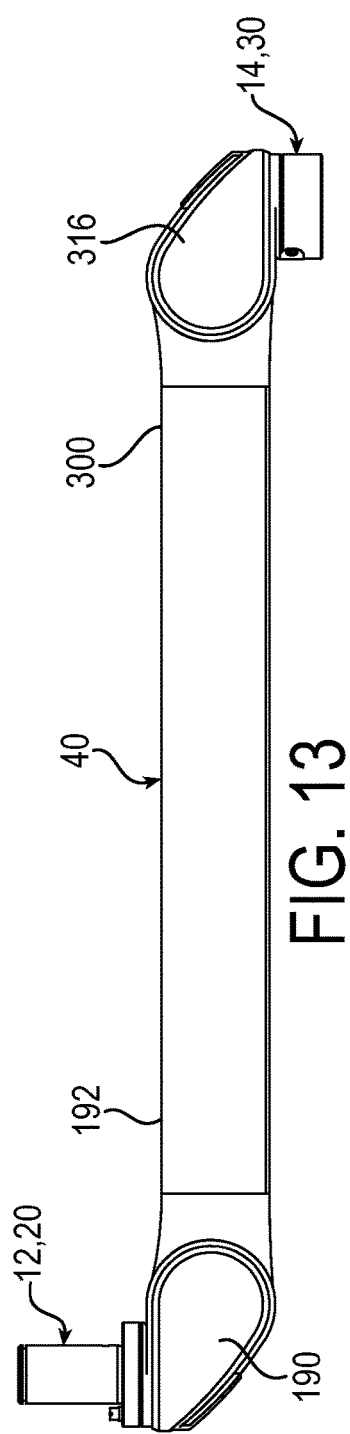

US 10,874,477 B2

MODULAR ADAPTERS FOR MEDICAL DEVICE SUPPORT SYSTEM

This application claims priority to U.S. Patent Application No. 62/799,096 filed Jan. 31, 2019; U.S. Patent Application No. 62/799,100 filed Jan. 31, 2019; U.S. Patent Application No. 62/799,113 filed Jan. 31, 2019; and U.S. Patent Application No. 62/799,202 filed Jan. 31, 2019. These prior applications are incorporated herein by reference.

FIELD OF INVENTION

This application relates generally to modular adapters for a load balancing arm of a medical device support system or carry system for use in, for example, a hospital examination room, a clinic, a surgery room or an emergency room, and more particularly to modular adapters that enable the load balancing arm of the medical device support system to be compatible with multiple extension arms and multiple accessories.

BACKGROUND

Medical device support systems or carry systems are used in health treatment settings such as hospital examination rooms, clinics, surgery rooms and emergency rooms. These systems may suspend or support any variety of medical devices or accessories including surgical lights, supply consoles, patient monitors, camera detector heads, medical instruments, ventilator systems, suction devices, among others. The support systems typically include a central shaft or support column that is suspended from the ceiling or mounted to a wall, one or more generally horizontal extension arms mounted for rotational movement about the shaft, and one or more load balancing arms, also known as spring arms or counterbalancing arms, that enable positioning of a medical device or accessory to a proper orientation relative to for example a patient operating table and healthcare professionals in the operating room.

The inventor has found that load balancing arms in some medical device support systems or carry systems have various shortcomings, drawbacks, and disadvantages relative to certain applications. For example, the load balancing arm may have dedicated proximal and distal end interfaces; that is, their proximal and distal end interfaces are integrally part of the load balancing arm structure, for example, part of the proximal and distal end hub structures of the load balancing arm. Thus, the hardware associated with a particular load balancing arm, for example the springs, housings, support structure, etc., that is compatible with one horizontal extension arm and set of accessories is incompatible with an extension arm and set of accessories of a different medical device support system. Incompatibilities can range from the interface connection, the size and/or geometry of the rotating and/or connecting components, and/or the load capability of the spring. The load balancing arms of different systems often require different components and different methods of mounting to their respective horizontal extension arms and accessories. Correspondingly, accessories that are compatible with the distal end of one load balancing arm will not always be compatible with a different load balancing arm.

Accordingly, there remains a need for further contributions in this area of technology.

SUMMARY OF INVENTION

The application relates to medical device support system adapters for connection to a load balancing arm of a medical device support system. The modular adapters enable the load balancing arm to be compatible with multiple extension arms and multiple accessories of a plurality of different medical device support systems.

According to one aspect of the invention, a medical device support system adapter for connection to a load balancing arm of a medical device support system, includes a body having a central axis; a connection component at one end of the body that is rotatably connectable to another component of the medical device support system; an interface at an opposite end of the body that is connectable to a hub of the load balancing arm of the medical device support system; wherein the interface has at least two mounting bolt holes equally angularly spaced apart about the central axis such that the body is connectable to the hub of the load balancing arm in at least two different angular positions of the body about the central axis.

Embodiments of the invention may include one or more of the following additional features separately or in combination.

The connection component may include a drop tube that is rotatably connectable to a support structure of the medical device support system.

The connection component may include a bearing support that is rotatably connectable to an accessory of the medical device support system.

The at least two mounting bolt holes may be on a bolt circle having the central axis as its center.

The at least two mounting bolt holes may include mounting bolt clearance holes.

The mounting bolt clearance holes may be counterbored.

The adapter may further include an annular structure that is mateable with a corresponding annular structure of the hub to axially align the adapter with the hub.

The annular structure of the adapter may include an annular protuberance and the annular structure of the hub may include an annular recess.

The annular structures may be circular shape.

The adapter may further include at least one rotational stop protruding from a portion of the one end and radially offset from the central axis.

The interface may have four mounting bolt holes equally angularly spaced apart about the central axis 90 degrees apart such that the body is connectable to the hub of the load balancing arm in four different angular positions of the body about the central axis.

According to another aspect of the invention, an adapter for a load balancing arm of a medical device support system includes a body having a central axis; a drop tube at one end of the body that is rotatably connectable to a support structure of the medical device support system; at least one rotational stop protruding from a portion of the one end and radially offset from the central axis; and, an interface at an opposite end of the body that is connectable to a hub of the load balancing arm.

Embodiments of the invention may include one or more of the following additional features separately or in combination.

The interface may have at least two mounting bolt holes equally angularly spaced apart about the central axis such that the body is connectable to the hub of the load balancing arm in at least two different angular positions of the body about the central axis.

The at least two mounting bolt holes may be on a bolt circle having the central axis as its center.

The rotational stop may be angularly offset from the at least two mounting bolt holes.

The adapter may be combined with a support structure of a medical device support system, wherein the support structure includes a horizontal extension arm, and wherein the drop tube is rotatably connectable to a knuckle joint assembly of the horizontal extension arm.

The drop tube may include a spindle with a circular groove to radially receive a retaining clip to axially support the drop tube.

According to another aspect of the invention, an adapter for a load balancing arm of a medical device support system includes a body having a central axis; a bearing support at one end of the body that is rotatably connectable to an accessory of the medical device support system; at least one rotational stop protruding from a portion of the one end and radially offset from the central axis; and an interface at an opposite end of the body that is connectable to a hub of the load balancing arm.

Embodiments of the invention may include one or more of the following additional features separately or in combination.

The interface may have at least two mounting bolt holes equally angularly spaced apart about the central axis such that the body is connectable to the hub of the load balancing arm in at least two different angular positions of the body about the central axis.

The at least two mounting bolt holes may be on a bolt circle having the central axis as its center.

The rotational stop may be angularly offset from the at least two mounting bolt holes.

The adapter may be combined with an accessory of a medical device support system, wherein the accessory includes an accessory spindle, and wherein the bearing support is rotatably connectable to the accessory spindle of the accessory.

The body may include a radial groove to radially receive a retaining clip to axially support the accessory.

According to another aspect of the invention, an interchangeable load balancing arm assembly for a medical device support system includes a load balancing arm having at least one hub; and, a plurality of interchangeable adapters that are attachable and detachable to the hub, wherein each of the plurality of interchangeable adapters includes a connection component having an associated connection component diameter and being rotatably connectable about an axis of rotation to another component of the medical device support system; wherein the plurality of interchangeable adapters have different axial lengths and/or different associated connection component diameters.

Embodiments of the invention may include one or more of the following additional features separately or in combination.

Each of the plurality of adapters may include a body having a central axis, and the connection component may be provided at one end of the body and an interface may be provided at an opposite end of the body, and the plurality of adapters may be attachable and detachable to the hub of the load balancing arm via the interface.

The interface may have at least two mounting bolt holes equally angularly spaced apart about the central axis such that the body is connectable to the hub of the load balancing arm in at least two different angular positions of the body about the central axis.

The at least one hub may include a proximal hub and a distal hub, and the plurality of interchangeable adapters may include a plurality of interchangeable drop tube adapters that are attachable and detachable to the proximal hub and a plurality of interchangeable bearing support adapters that are attachable and detachable to the distal hub.

The plurality of interchangeable adapters may include respectively a plurality of interchangeable drop tube adapters, and each interchangeable drop tube adapter may include a drop tube that is rotatably connectable to a support structure of the medical device support system, and the drop tubes of the plurality of interchangeable drop tube adapters may have different axial lengths and/or different associated drop tube diameters.

The plurality of interchangeable adapters may include respectively a plurality of interchangeable bearing support adapters, and each interchangeable bearing support adapter may include a bearing support that is rotatably connectable to an accessory of the medical device support system, and the bearing supports of the plurality of interchangeable bearing support adapters may have different axial lengths and/or different associated bearing support diameters.

The at least one hub may include a proximal hub and a distal hub, and the proximal hub may include a first outer hub portion and the distal hub may include a second outer hub portion, and the first and second outer hub portions may have a one part geometry.

The following description and the annexed drawings set forth certain illustrative embodiments of the invention. These embodiments are indicative, however, of but a few of the various ways in which the principles of the invention may be employed. Other objects, advantages and novel features according to aspects of the invention will become apparent from the following detailed description when considered in conjunction with the drawings.

BRIEF DESCRIPTION OF THE DRAWINGS

The annexed drawings, which are not necessarily to scale, show various aspects of the invention.

FIG. 8 is a top perspective view of the proximal end of the load balancing arm, showing a proximal hub and proximal hub interface.

FIG. 9 is a top plan view of a proximal end adapter and a top plan view of a proximal end of a load balancing arm, offset from one another, showing an interface of each in accordance with an embodiment of the invention.

FIG. 12 is a side view of a load balancing arm, three different proximal end adapters, and two different distal end adapter, in accordance with an embodiment of the invention.

FIG. 13 is a side view of a load balancing arm with a proximal end adapter and a distal end adapter connected to the load balancing arm.

DETAILED DESCRIPTION

Figure 1:
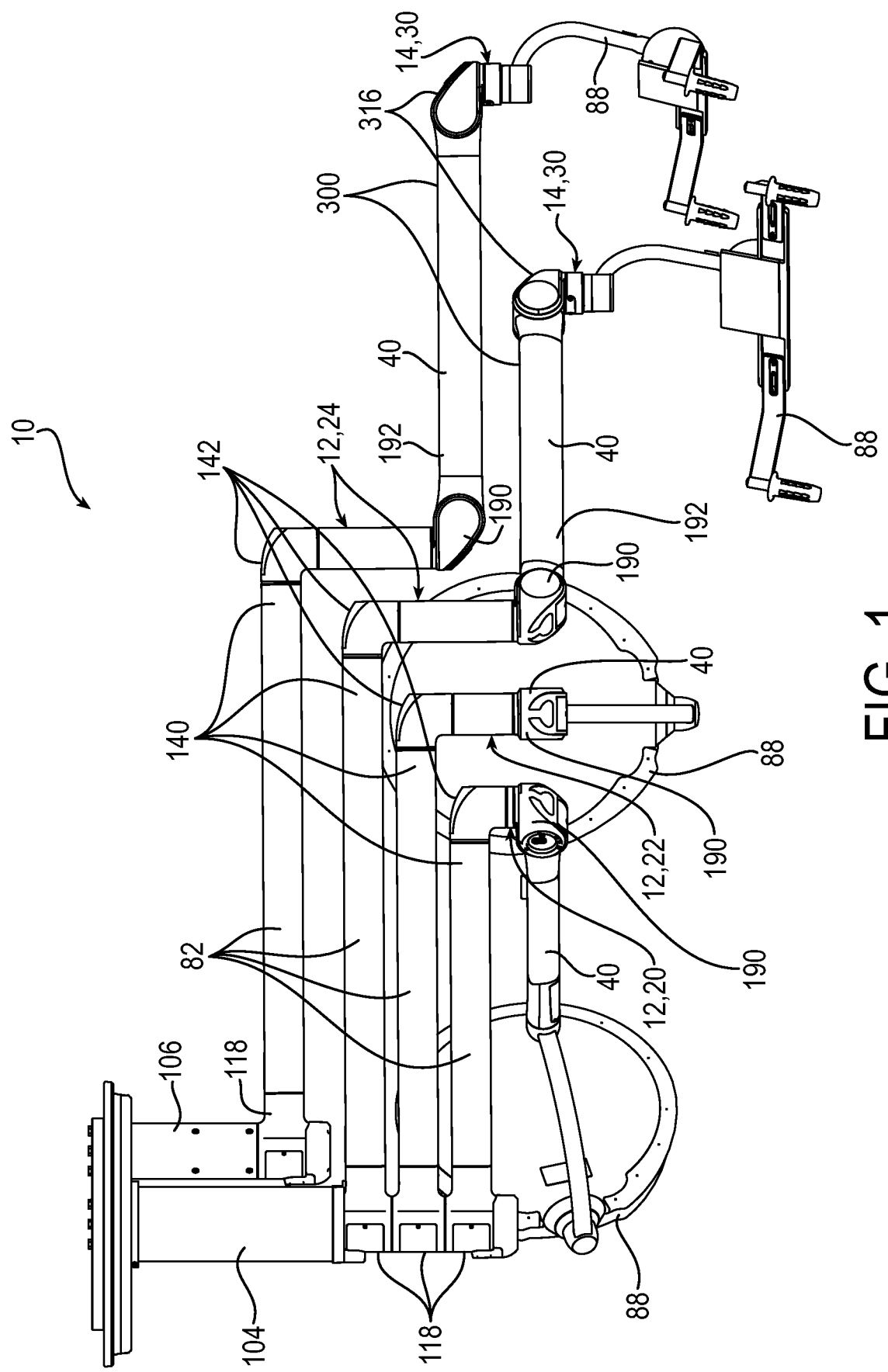
FIG. 1 is a perspective view of a medical device support system in accordance with an embodiment of the invention.

While the present invention can take many different forms, for the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications of the described embodiments, and any further applications of the principles of the invention as described herein, are contemplated as would normally occur to one skilled in the art to which the invention relates.

Figure 2:
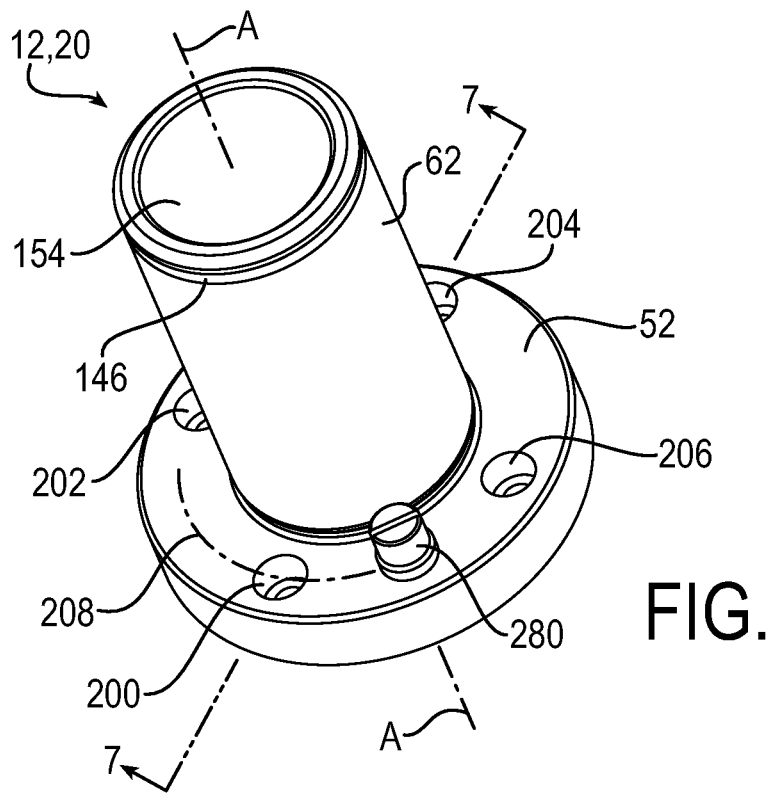
FIG. 2 is a top perspective view of a proximal end adapter in accordance with an embodiment of the invention, showing a drop tube, rotational stop, and mounting bolt holes.
Figure 3:
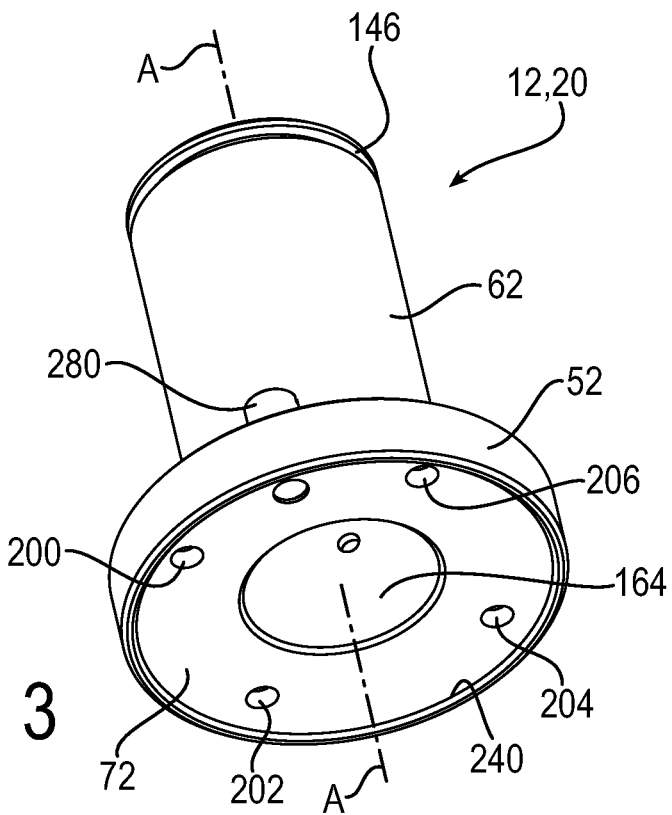
FIG. 3 is a bottom perspective view of the FIG. 2 proximal end adapter.
Figure 4:
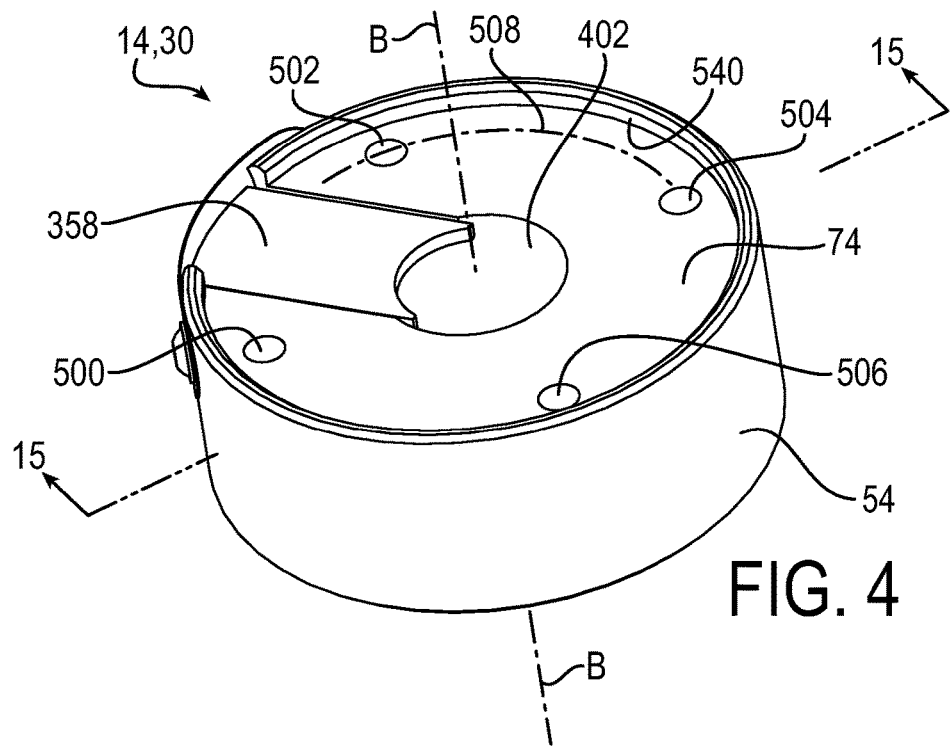
FIG. 4 is a top perspective view of a distal end adapter in accordance with an embodiment of the invention, showing a retaining clip guideway, bearing support and mounting bolt holes.
Figure 5:
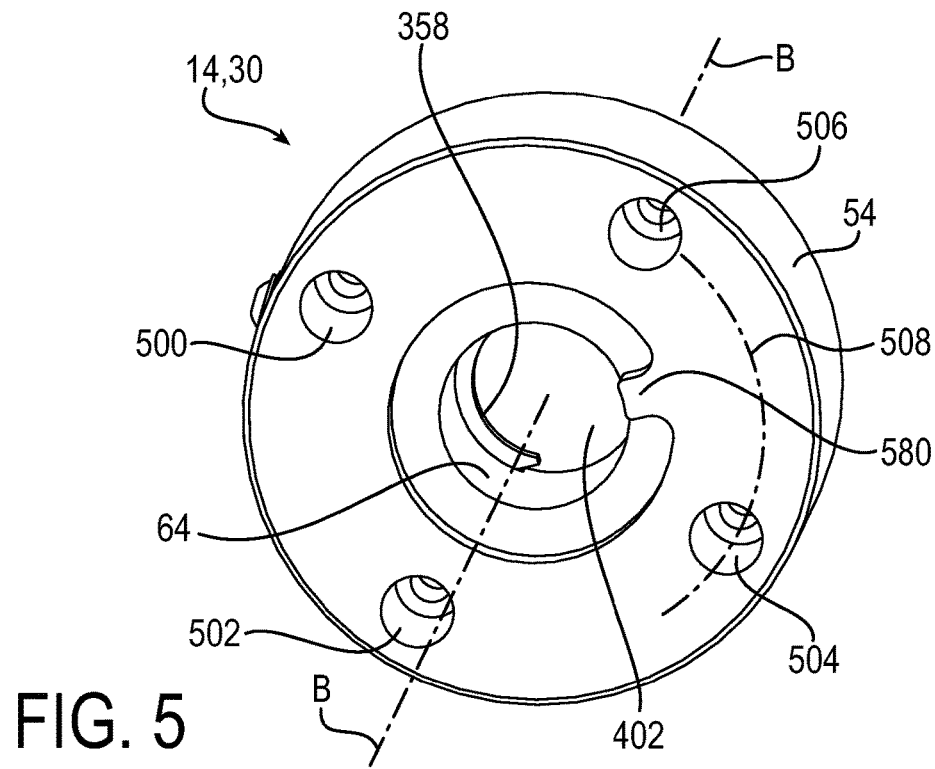
FIG. 5 is a bottom perspective view of the FIG. 4 distal end adapter, showing a rotational stop and mounting bolt holes.

FIGS. 1-5 show a medical device support system 10 including three non-integral proximal end adapters 12 and two non-integral distal end adapters 14 in accordance with an embodiment of the invention. The three proximal end adapters 12 are referenced herein more particularly as adapters 20, 22, 24, the adapter 20 of which is shown in FIGS. 2 and 3. The two distal end adapters 14 are referenced herein more particularly as 30, 32, the adapter 30 of which is shown in FIGS. 4 and 5. The proximal end adapters 12 and distal end adapters 14 are removably connected to the respective proximal and distal ends of load balancing arms 40 of the medical device support system 10. As shown in FIGS. 2-5, the adapters 12, 14 include respectively a body 52, 54 having a central axis A-A, B-B, a connection component 62, 64 at one end of the body 52, 54 that is rotatably connectable to another component of the medical device support system 10, and an interface 72, 74 at an opposite end of the body 52, 54 that is connectable to a hub of the load balancing arm 40. As will be described in greater detail below, the load balancing arms 40 are not limited to a single dedicated connection interface at the proximal end or distal end. Rather, as shown in FIG. 1, the proximal end adapters 12 enable the load balancing arm 40 to be connected to for example any number of different horizontal extension arms 82 of medical device support systems; and, the distal end adapters 14 enable the load balancing arm 40 to be connected to for example any number of different accessories 88 of medical device support systems.

The illustrated medical device support system 10 includes a central shaft or support column 104 and a radially offset shaft or support column 106 that are suspended from the ceiling. Four generally horizontal extension arms 82 are mounted to the shafts 104, 106 for rotational movement about the shafts 104, 106 via proximal hubs 118 of the extension arms 82. The shafts 104, 106 could be mounted to a wall or stand rather than the ceiling. The four load balancing arms 40, which are also referred to as counter-balancing arms, are mounted to the respective extension arms 82. The load balancing arms 40 enable positioning of a medical device load 88 or accessory 88 to a proper orientation relative to for example a patient operating table and healthcare professionals in the operating room. Further details of a suitable load balancing arm are described in U.S. Provisional Patent Application No. 62/799,202, filed Jan. 31, 2019, and titled "Load Balancing Arm for Medical Device Support System," and U.S. Provisional Patent Application No. 62/799,113, filed Jan. 31, 2019, and titled "Support Arm for Medical Device Support System," which are incorporated by reference for all purposes as if fully set forth herein.

Figure 6:
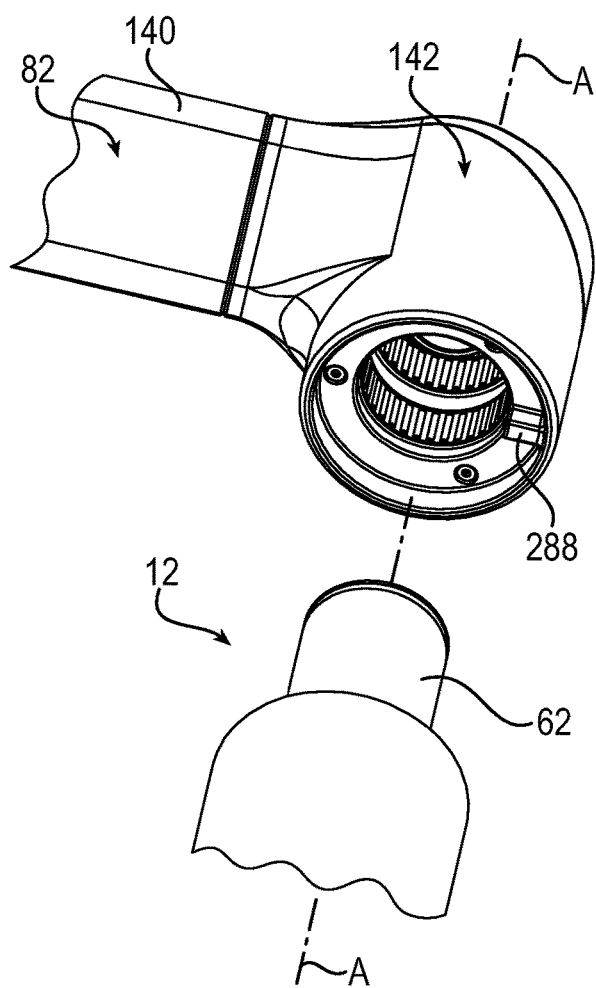
FIG. 6 is an exploded bottom perspective view of a distal end of a horizontal extension arm and a proximal end adapter.
Figure 7:
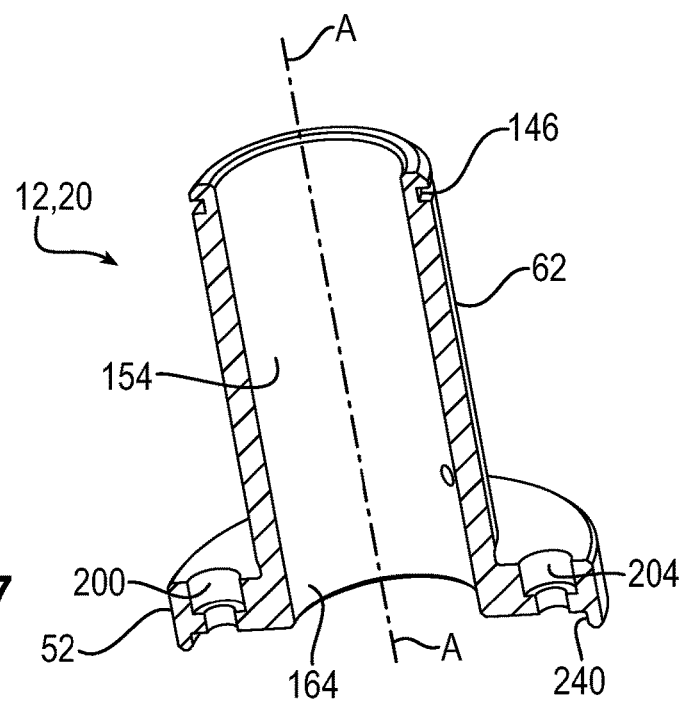
FIG. 7 is a cross section view of the FIG. 2 proximal end adapter as viewed from the plane 7-7 in FIG. 2.

Referring to FIGS. 1-3 and 6-8, the extension arms 82 each include at their distal end 140 a knuckle joint assembly 142 that rotatably supports the connection component 62 of the proximal end adapter 12. In the illustrative embodiment, the connection component 62 includes a drop tube 62 that serves as a rotatable spindle 62 and a passage for routing support system functional components. The knuckle joint assembly 142 rotatably supports the drop tube spindle 62 and thus the load balancing arm 40 to which it is connected about the central axis A-A. As shown in FIGS. 2, 3 and 7, the spindle 62 may include a circular groove 146 in its outer surface near the distal end of the spindle 62. A retaining clip (not shown) may be provided that is movable radially inward and radially outward relative to the central axis A-A to respectively engage and disengage the groove 146 in the drop tube spindle 62. In the engaged position, the retaining clip rotatably supports the spindle 62 in an axial position along the central axis A-A. In the disengaged position, the retaining clip is disengaged from the groove 146 to allow movement of the spindle 62 along the central axis A-A, for example, to remove the spindle 62 and thus release the load balancing arm 40 from the knuckle joint assembly 142. The retaining clip may be guided for radially inward and radially outward movement by a guide surface or slot (not shown) inside a housing structure of the knuckle joint assembly 142. Further details of a suitable knuckle joint assembly and retaining clip are described in U.S. Provisional Patent Application No. 62/799,096, filed Jan. 31, 2019, and titled "Knuckle Joint Assembly for Medical Device Support System," which is incorporated by reference for all purposes as if fully set forth herein.

The drop tube connection component 62 also serves as a passage to route functional components. As shown in FIGS. 2 and 7, the drop tube 62 has an axially extending cavity 154. The illustrative cavity 154 has a cylindrical shape although other shapes are contemplated, for example a cylindrical shape with radially inwardly projecting ribs or connection bosses. The body 52 of the proximate end adapter 12 also has an axially extending cavity 164. The as-shown cavity 164 is cylindrical in shape although, like the cavity 154 of the drop tube 62, can be other than cylindrical in shape. The cavity 164 coincides with, or extends along the same central axis A-A as, the cavity 154 of the drop tube 62. In the embodiment of FIGS. 2, 3 and 7, the cavities 154, 164 have the same size diameter although as will be described in greater detail below different size diameters are also contemplated. Referring to FIG. 1, the cavities 154, 164 enable cables, tubes, etc. to be routed from the extension arm 82, through the knuckle joint assembly 142, through the proximal end adapter 12, and into the load balancing arm 40. In some embodiments, the cavities 154, 164 may also house slip rings, commutators, among other components.

Turning now to FIGS. 1-3 and 7-9, the proximal end adapter 12 is connected to a proximal hub 190 at the proximal end 192 of the load balancing arm 40. To facilitate this connection, the interface 72 of the proximal end adapter 12 has a plurality of mounting bolt holes 200, 202, 204, 206 on an adapter bolt circle 208 and an interface 220 of the proximal hub 190 has a plurality of mounting bolt holes 230, 232, 234, 236 on a proximal hub bolt circle 238. The adapter bolt circle 208 and the proximal hub bolt circle 238 have the same diameter. As shown in FIGS. 2, 3, 7 and 8, the mounting bolt holes 200, 202, 204, 206 of the proximal end adapter 12 are clearance holes that are counterbored, and the mounting bolt holes 230, 232, 234, 236 of the proximal hub 190 are threaded holes.

To fasten the proximal end adapter 12 to the proximal hub 190 the plurality of mounting bolt holes 200, 202, 204, 206 are axially aligned with the plurality of mounting bolt holes 230, 232, 234, 236. To aid in such axial alignment, the proximal end adapter 12 includes an annular circular shape convex section or protuberance 240 that mates with a corresponding annular circular shape concave section or recess 242 in the proximal hub 190. The annular protuberance 240 coincides with the annular groove 242 along the central axis A-A. As shown in FIG. 3, the annular protuberance 240 projects from the body 52 of the proximal end adapter 12 in a direction opposite the connection component 62 (downward in FIG. 1). As shown in FIGS. 8 and 9, the annular recess 242 surrounds an annular ledge 244 of the interface 220 of the proximal hub 190 and is recessed from the upper surface of the interface 220 in a direction away from the proximal end adapter 12 (downward in FIG. 1). The annular protuberance 240 has an inner diameter that is slightly larger than an outer diameter of the ledge 244 of the interface 220. As the proximal end adapter 12 is installed on the proximal hub 190, the annular ledge 244 guides the annular protuberance 240 to align the adapter bolt circle 208 and proximal hub bolt circle 238 of the respective mounting bolt clearance holes 200, 202, 204, 206 and mounting bolt threaded holes 230, 232, 234, 236. The proximal end adapter 12 can then be rotated relative to the proximal hub 190 to axially align the mounting bolt clearance holes 200, 202, 204, 206 with the mounting bolt threaded holes 230, 232, 234, 236.

It will be appreciated that the axial alignment of the bolt circles 208, 238 need not be limited to the proximal end adapter 12 having the annular circular shape convex section or protuberance 240 and the proximal hub 190 having the corresponding annular circular shape concave section or recess 242. The converse also is possible; that is, the proximal hub 190 may include an annular circular shape convex section or protuberance that mates with a corresponding annular circular shape concave section or recess in the proximal end adapter 12. Also, the annular protuberance 240 and annular recess 242 may be other than circular in shape, for example, a regular polygon shape or the like. It will further be appreciated that although in the illustrative embodiment the annular protuberance 240 and annular recess 242 are radially outward from the respective bolt circles 208, 238, in an alternate embodiment the annular protuberance 240 and annular recess 242 may be radially inward of the respective bolt circles 208, 238.

Once aligned, mounting bolts, more specifically shoulder bolts, may be inserted through the mounting bolt clearance holes 200, 202, 204, 206 and threaded into the mounting bolt threaded holes 230, 232, 234, 236 and tightened to an appropriate torque. The drop tube connection component 62 is then connected to the proximal hub 190 of the load balancing arm 40 and may then be slidably inserted into the knuckle joint assembly 142 and retained therein for rotatable movement relative thereto by engaging the afore described retaining clip in the groove 146.

In the illustrative embodiment, the proximal end adapter 12 has mounting bolt clearance holes 200, 202, 204, 206 that are counterbored, and the proximal hub 190 has mounting bolt threaded holes 230, 232, 234, 236. The invention is not so limited and other embodiments are contemplated. The mounting bolt clearance holes 200, 202, 204, 206 need not be counterbored; rather, the mounting bolt clearance holes 200, 202, 204, 206 may be straight bored and the head of the mounting bolts may instead engage the upper surface of the interface 72 of the proximal end adapter 12. In an embodiment, the proximal end adapter 12 may have mounting bolt threaded holes, and the proximal hub 190 may have mounting bolt clearance holes. To access mounting clearance holes in the proximal hub 190, one or more cover plates 252 may be removed from the underlying structure of the proximal hub 190. In another embodiment, the proximal end adapter 12 may have a combination of mounting bolt clearance holes and mounting bolt threaded holes, and the proximal hub 190 may have a combination of mounting bolt clearance holes and mounting bolt threaded holes. In still a further embodiment, both the proximal end adapter 12 and the proximal hub 190 have mounting bolt clearance holes, and threaded mounting bolts are passed through the holes and secured into place by means of a nut or the like.

The as-shown proximal end adapter 12 has four mounting bolt holes 200, 202, 204, 206 and the as shown proximal hub 190 similarly has four mounting bolt holes 230, 232, 234, 236. Other quantities are also envisaged although the proximal end adapter 12 and proximal hub 190 should have at least two mounting bolt holes for appropriate load distribution between the two components. Thus, two, three, five, or more, mounting bolt holes may be suitable. It will also be appreciated that the proximal end adapter 12 may have fewer or a greater quantity of mounting bolt holes than the proximal hub 190. For example, the proximal end adapter 12 may have two mounting bolt holes and the proximal hub 190 may have two, four, six or eight mounting bolt holes, or other multiples of two. The proximal end adapter 12 may have three mounting bolt holes and the proximal hub 190 may have three, six, or nine mounting bolt holes, or other multiples of three.

The four mounting bolt holes 200, 202, 204, 206 of the proximal end adapter 12 are equally angularly spaced apart about the central axis A-A, as are the four mounting bolt holes 230, 232, 234, 236 of the proximal hub 190 of the load balancing arm 40. Thus, the body 52 of the proximal end adapter 12 may be connected to the proximal hub 190 in at least four different angular positions of the body 52 about the central axis A-A. In this regard, the four mounting bolt holes 200, 202, 204, 206 may be aligned respectively with the four mounting bolt holes 230, 232, 234, 236 for a first angular position; or aligned respectively with the four mounting bolt holes 232, 234, 236, 230 for a second angular position that is 90 degrees away from the first angular position; or aligned respectively with the four mounting bolt holes 234, 236, 230, 232 for a third angular position that is 180 degrees away from the first angular position; or aligned respectively with the four mounting bolt holes 236, 230, 232, 234 for a fourth angular position that is 270 degrees away from the first angular position.

Other embodiments are also contemplated. Thus, the interface 72 of the proximal end adapter 12 may have two or more mounting bolt holes (two, three, four, five, or more) equally angularly spaced apart about the central axis A-A such that the body 52 is connectable to the proximal hub 190 of the load balancing arm 40 in at least two different angular positions of the body 52 about the central axis A-A. For two equally angularly spaced apart mounting bolt holes in the proximal end adapter 12 and the proximal hub 190, the body 52 of the proximal end adapter 12 may be connected to the proximal hub 190 in two different angular positions of the body 52 about the central axis A-A, where the second angular position is 180 degrees away from the first angular position. For three equally angularly spaced apart mounting bolt holes in the proximal end adapter 12 and the proximal hub 190, the body 52 of the proximal end adapter 12 may be connected to the proximal hub 190 in three different angular positions of the body 52 about the central axis A-A, where the second angular position is 120 degrees away from the first angular position, and the third angular position is 120 degrees away from the second angular position. For five holes, the angular spacing would be 72 degrees; for six holes, the angular spacing would be 60 degrees; and so on.

In the illustrative embodiment, the proximal end adapter 12 and the proximal hub 190 each have a single respective bolt circle 208, 238, and the bolt circles 208, 238 have the same diameter. As will be appreciated, the proximal end adapter 12 and/or the proximal hub 190 may have multiple bolt circles and some of the bolt circles may be on different diameters. For example, the proximal end adapter 12 may have not only the mounting bolt holes 200, 202, 204, 206 on the adapter bolt circle 208 that are mateable with the mounting bolt holes 230, 232, 234, 236 on the proximal hub 190, but also a different set of mounting bolt holes on a different adapter bolt circle that are mateable with mounting bolt holes on a different proximal hub.

Referring to FIGS. 2, 3, 6 and 9, the proximal end adapter 12 may include one or more rotational stops, one rotational stop 280 in the illustrative embodiment, that protrudes from a portion of the connection component 62 end of the body 52 and is radially offset from the central axis A-A. As shown in FIGS. 2 and 9, the rotational stop 280 is angularly offset from the mounting bolt holes 200, 202, 204, 206. The rotational stop 280, as its name suggests, stops rotation of the load balancing arm 40 relative to the knuckle joint assembly 142 at the distal end 140 of the extension arm 82. As shown in FIG. 6, the knuckle joint assembly 142 includes a corresponding rotational stop 288 that lies in the same plane perpendicular to the central axis A-A as the rotational stop 280 when the proximal end adapter 12 is installed in the knuckle joint assembly 142. As will be appreciated, the rotational stop 288 permits approximately a 340 degree range of rotational movement (assuming each rotational stop 280, 288 has a 10 degree angular footprint) of the load balancing arm 40 relative to the distal end 140 of the extension arm 82 about the central axis A-A. Additional rotational stops can be employed in the proximal end adapter 12 and/or the knuckle joint housing 142 to limit the rotation of the load balancing arm 40 relative to the extension arm 82 to any necessary or desired angular range.

In an embodiment, the one or more rotational stops 288 can be configured to be removable. Further, the proximal end adapter 12 may have a plurality of mounting holes into which to insert the rotational stops 288. For continuous rotation applications, for example as may be the case where the rotation of the load balancing arm relative to the horizontal extension arm is by other stop means, the rotational stop can be removed from the proximal end adapter 12, or omitted from the construction of the proximal end adapter 12.

Figure 10:
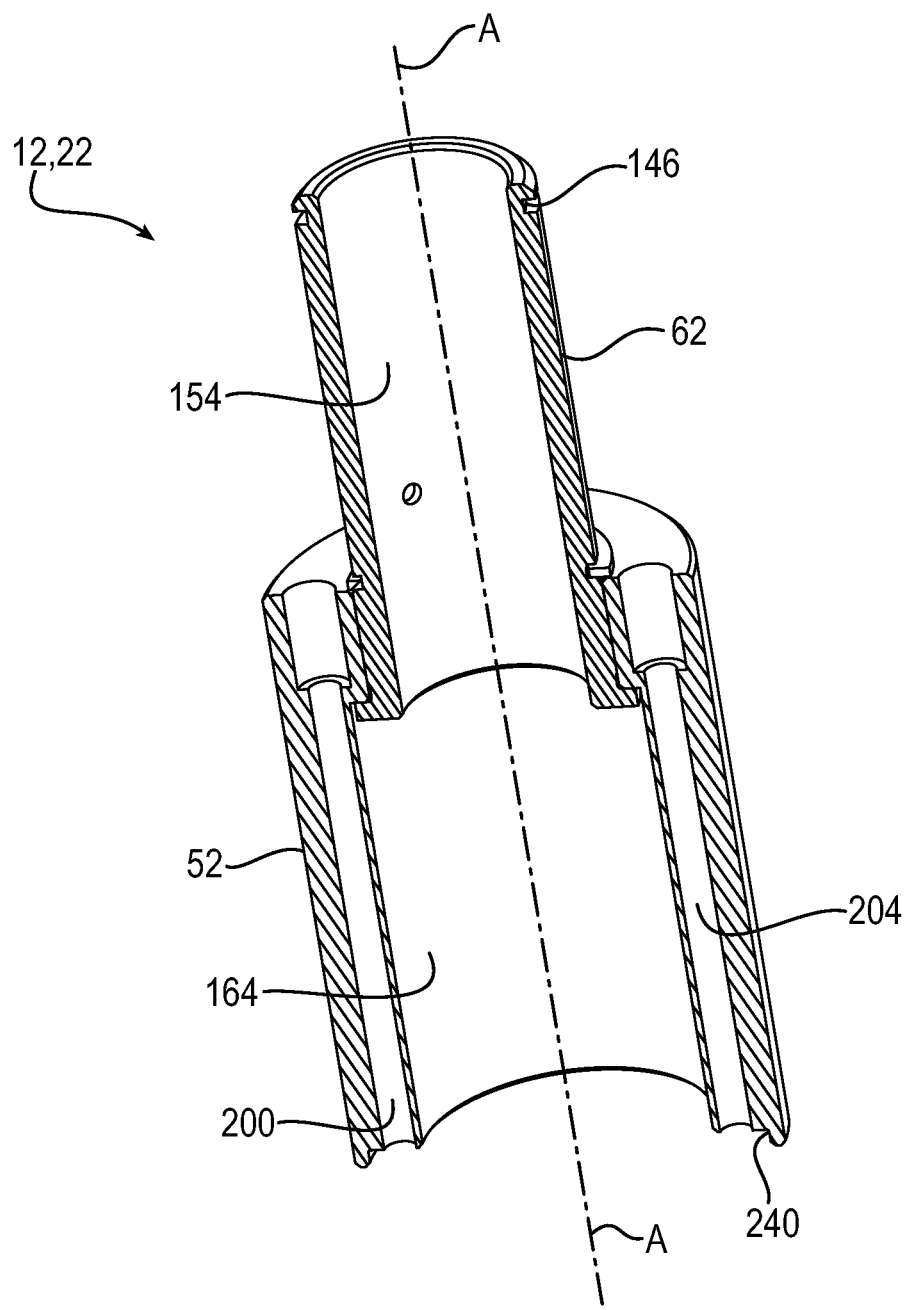
FIG. 10 is a cross section view of a proximal end adapter in accordance with another embodiment of the invention.
Figure 11:
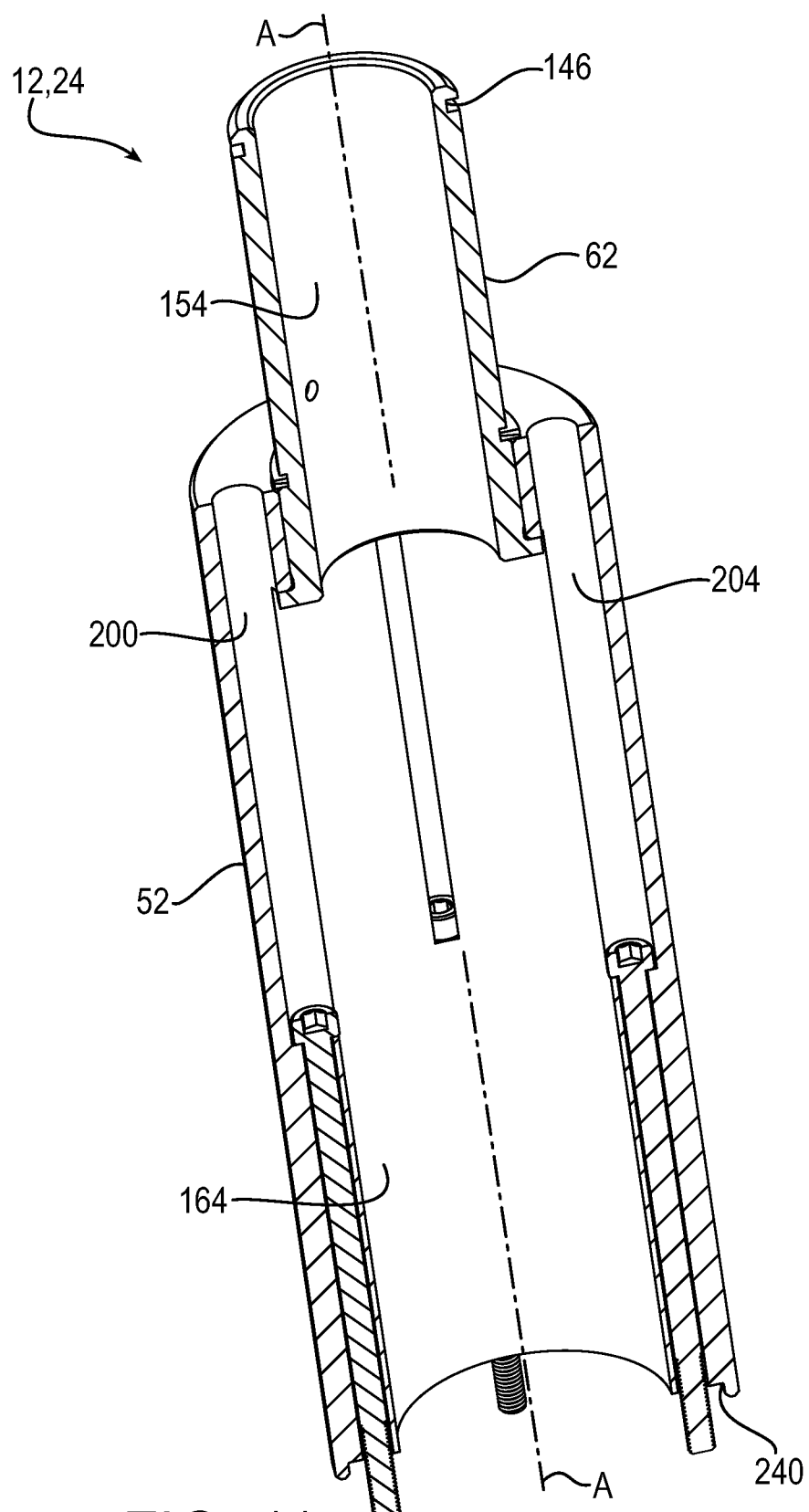
FIG. 11 is a cross section view of a proximal end adapter in accordance with another embodiment of the invention.

FIGS. 1, 10 and 11 show proximal end adapters 12, 22 and 12, 24 in accordance with additional embodiments of the invention. The FIG. 10 proximal end adapter 12, 22 differs from the FIG. 7 proximal end adapter 12, 20 in that the proximal end adapters 12, 22 and 12, 24 have longer axial dimensions, and the cavities 154, 164 have the different size diameters. Thus, the proximal end adapters 22, 24 are mateable to the proximal hub 190 of the load balancing arm 40 in the same manner as described above with respect to the proximal end adapter 12, 20. As will be appreciated, because the load balancing arm 40 can be mated with any one of the three proximal end adapters 20, 22, 24, the load balancing arm 40 is not limited to a single dedicated connection interface at its proximal end.

FIGS. 12 and 13 illustrate a load balancing arm 40 with some of the available options for proximal end adapters 20, 22, 24, three in the illustrative embodiment, with FIG. 13 showing the proximal end adapter 20 connected to the proximal hub 190 of the load balancing arm 40. The proximal end adapters 20, 22, 24 shown can be said to represent a short drop tube adapter 20, a medium drop tube adapter 22, and a long drop tube adapter 24. As shown in FIG. 1, the three different length drop tube adapters 20, 22, 24 enable the same load balancing arm 40, that is the three load balancing arms 40 coupled to the support column 104 via respective extension arms 82, to be at even knuckle height elevations on the medical device support system 10. Thus, when oriented horizontally as shown, the load balancing arms 40 rotate in the same knuckle elevation plane relative to the floor.

The proximal end adapter 12 may be constructed to provide options other than different lengths. In an embodiment, three proximal end adapters 12 may have three different diameters of drop tube connection component 62. This would enable the load balancing arm 40 to be rotatably connectable to, for example, three different knuckle joint assemblies of three different extension arms of three different medical device support systems. Thus, for example, a first proximal end adapter may have a first relatively small diameter drop tube connection component 62 that would be rotatably connectable to a first knuckle joint assembly having a relatively small diameter mating opening; a second proximal end adapter may have a second relatively medium size diameter drop tube connection component 62 that would be rotatably connectable to a second knuckle joint assembly having a relatively medium size diameter mating opening; and, a third proximal end adapter may have a third relatively large size diameter drop tube connection component 62 that would be rotatably connectable to a third knuckle joint assembly having a relatively large diameter mating opening. The same load balancing arm 40 would be mateable to three different extension arms of three different medical device support systems simply by the provision of three different proximal end adapters 12. As will be appreciated, this avoids the need for the manufacture of three different load balancing arms having their own proximal end drop tube connection interface integrally part of the load balancing arm structure.

Figure 14:
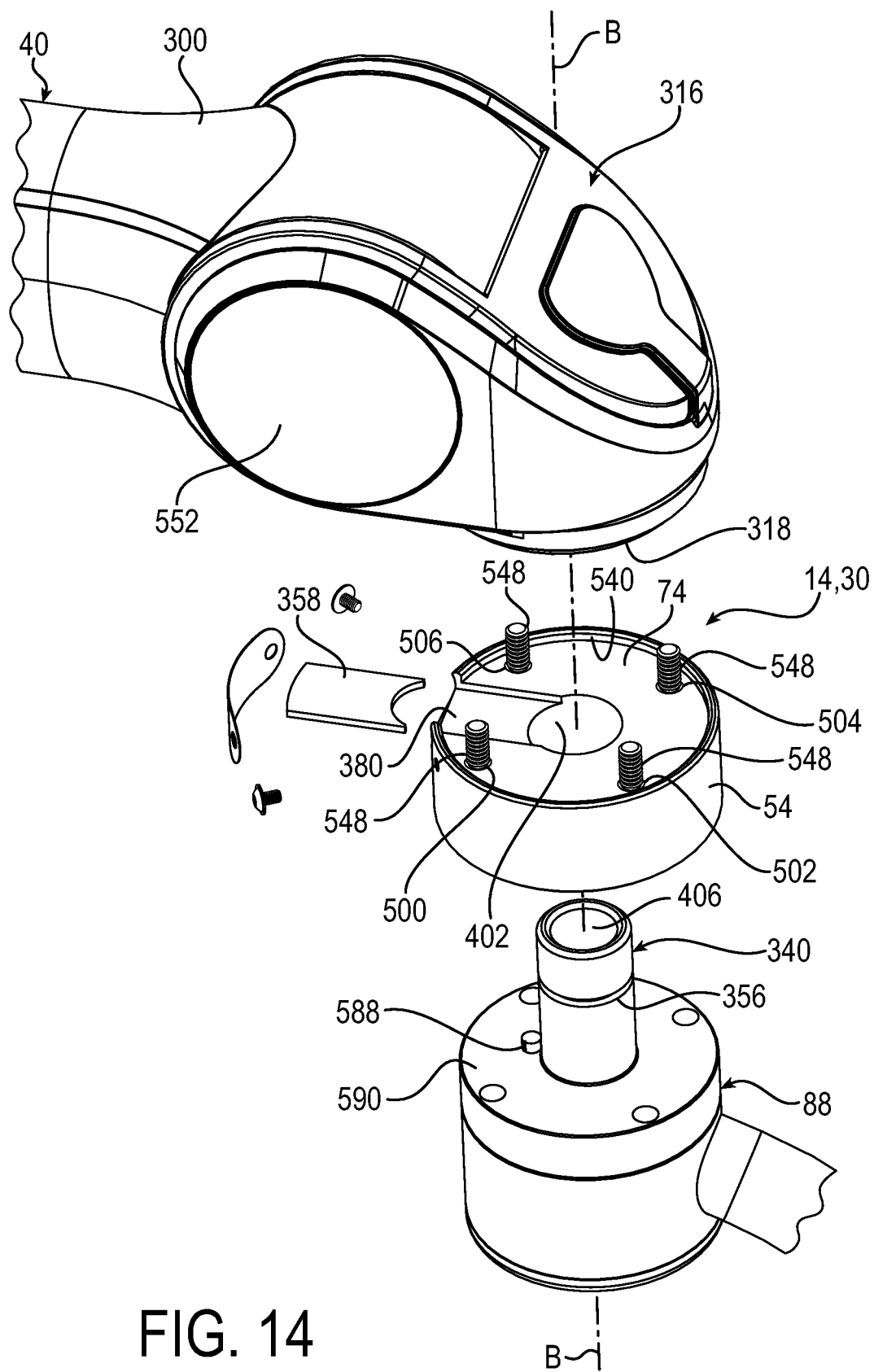
FIG. 14 is an exploded top perspective view of a distal end of a load balancing arm, a distal end adapter, and the proximal end of an accessory.
Figure 15:
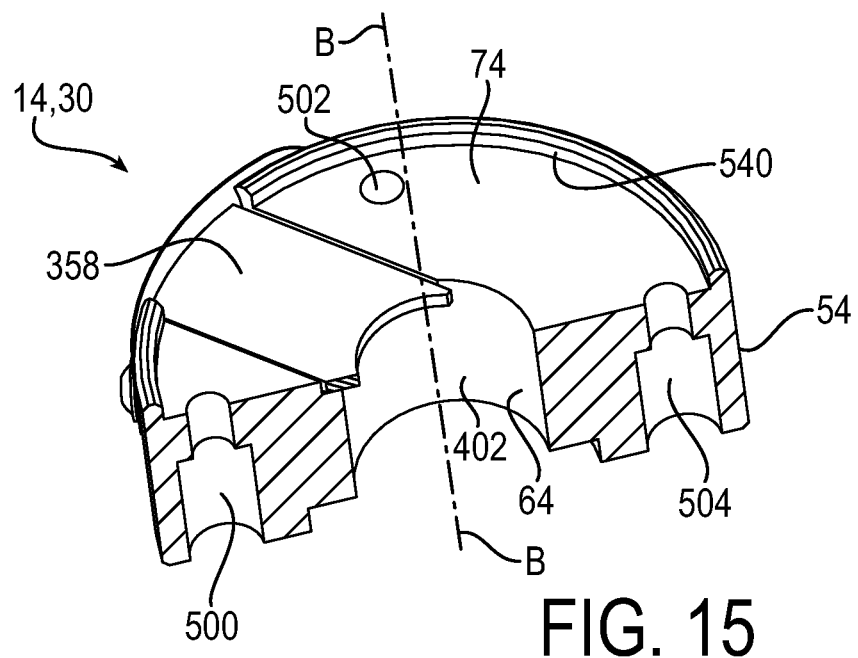
FIG. 15 is a cross section view of the FIG. 4 distal end adapter as viewed from the plane 15-15 in FIG. 4.

Referring now to FIGS. 1, 4, 5 and 14-16, the distal end adapter 14 will now be described. Two of the load balancing arms 40 shown in FIG. 1 (the right two) each include at their distal end 300 a distal hub 316. The distal hub 316 includes an interface 318 to which the distal end adapter 14 is mounted. The distal end adapter 14, in turn, includes a connection component 64 that is rotatably connected about a central axis B-B to an accessory 88 or medical device load 88 of the medical device support system 10. In the illustrative embodiment, the connection component 64 includes a bearing support 64 that serves as an opening for receiving an accessory spindle 340 and a passage for routing support system functional components. The distal end adapter 14 rotatably supports the accessory spindle 340 and thus the accessory 88 to which it is connected about the central axis B-B. As shown in FIG. 14, the accessory spindle 340 may include a circular groove 356 in its outer surface near the distal end of the accessory spindle 340. The distal end adapter 14 may include a retaining clip 358 that is movable radially inward and radially outward relative to the central axis B-B to respectively engage and disengage the groove 356 in the accessory spindle 340. In the engaged position, the retaining clip 358 rotatably supports the accessory spindle 340 in an axial position along the central axis B-B. In the disengaged position, the retaining clip 358 is disengaged from the groove 356 to allow movement of the accessory spindle 340 along the central axis B-B, for example, to remove the accessory spindle 340 and thus release the accessory 88 from the distal hub 316 of the load balancing arm 40. Referring to FIGS. 4, 14 and 15, the retaining clip 358 may be guided for radially inward and radially outward movement by a guide surface or slot 380 inside the body 54 of the distal end adapter 14. Further details of a suitable retaining clip are described in U.S. Provisional Patent Application No. 62/799,096, filed Jan. 31, 2019, and titled "Knuckle Joint Assembly for Medical Device Support System," which is incorporated by reference for all purposes as if fully set forth herein.

The medical device accessory 88 may include a patient monitor support as shown on the right side of FIG. 1, or a surgical light, a supply console, a camera detector head, a medical instrument, a ventilator system, a suction device, among others. In some embodiments, the distal end 300 of the load balancing arm 40 may be coupled directly to a medical device accessory 88, such as the surgical lights shown on two of the load balancing arms 40 (the left two) in FIG. 1, and thus without a distal end adapter. A control console, if provided, may provide controls for navigation of a medical instrument that is either coupled to or remote from the load balancing arm 40.

The bearing support connection component 64 of the distal end adapter 14 also serves as a passage to route functional components. As shown in FIGS. 4 and 5, the bearing support 64 has an axially extending cylindrical shape cavity 402 that extends along the central axis B-B. As shown in FIG. 14, the accessory spindle 340 also includes an axially extending cylindrical shape cavity 406 that extends along the central axis B-B and, when assembled to the bearing support 64, coincides with the cavity 402 of the distal end adapter 14. Referring to FIG. 14, the cavities 402, 406 enable cables, tubes, etc. to be routed from the load balancing arm 40, through the distal hub 316, through the distal end adapter 14, through the accessory spindle 340, and into the accessory 88. In some embodiments, the cavities 402, 406 may also house slip rings, commutators, among other components.

Turning now to FIGS. 1, 4, 5 and 14-16, the distal end adapter 14 is connected to the distal hub 316 of the load balancing arm 40. To facilitate this connection, the interface 74 of the distal end adapter 14 has a plurality of mounting bolt holes 500, 502, 504, 506 on an adapter bolt circle 508 and the interface 318 of the distal hub 316 has a plurality of mounting bolt holes 530, 532, 534, 536 on a distal hub bolt circle 538. The adapter bolt circle 508 and the distal hub bolt circle 538 have the same diameter. As shown in FIGS. 4, 5, 15 and 16, the mounting bolt holes 500, 502, 504, 506 of the distal end adapter 14 are clearance holes that are counterbored, and the mounting bolt holes 530, 532, 534, 536 of the distal hub 316 are threaded holes.

Figure 16:
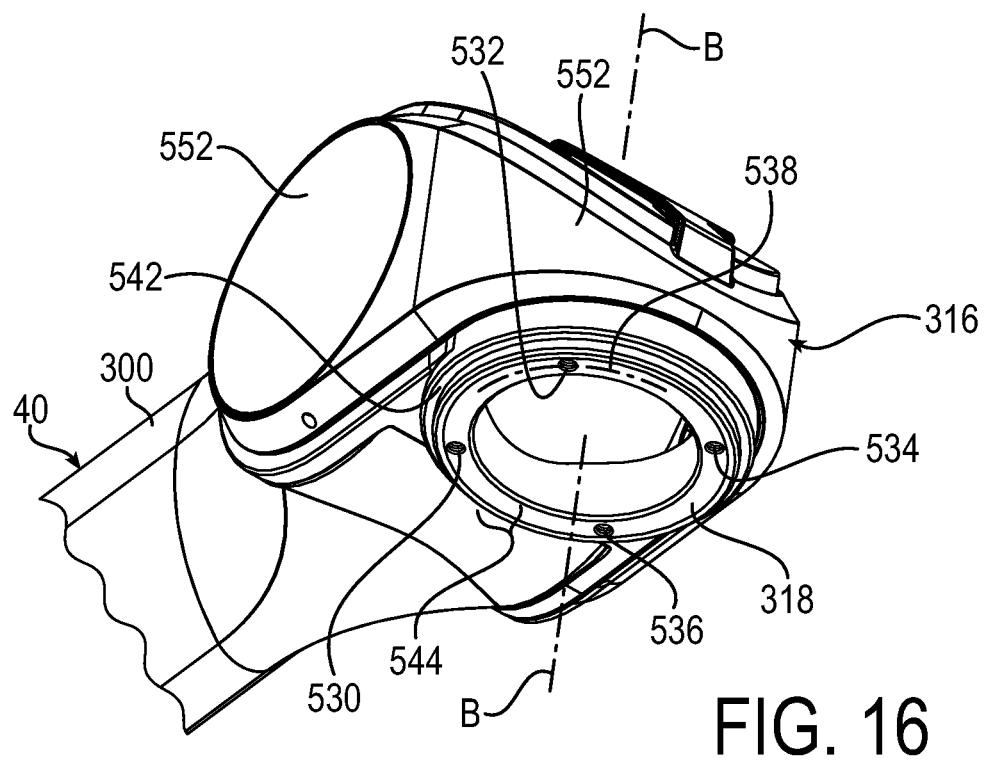
FIG. 16 is a bottom perspective view of the distal end of the load balancing arm, showing a distal hub and distal hub interface.

To fasten the distal end adapter 14 to the distal hub 316 the plurality of mounting bolt holes 500, 502, 504, 506 are axially aligned with the plurality of mounting bolt holes 530, 532, 534, 536. To aid in such axial alignment, the distal end adapter 14 includes an annular circular shape convex section or protuberance 540 that mates with a corresponding annular circular shape concave section or recess 542 in the distal hub 316. The annular protuberance 540 coincides with the annular groove 542 along the central axis B-B. As shown in FIG. 4, the annular protuberance 540 projects from the body 54 of the distal end adapter 14 in a direction opposite the connection component 64 (upward in FIG. 1). As shown in FIG. 16, the annular recess 542 surrounds an annular ledge 544 of the interface 318 of the distal hub 316 and is recessed from the upper surface of the interface 318 in a direction away from the distal end adapter 14 (upward in FIG. 1). The annular protuberance 540 has an inner diameter that is slightly larger than an outer diameter of the ledge 544 of the interface 318. As the distal end adapter 14 is installed on the distal hub 316, the annular ledge 544 guides the annular protuberance 540 to align the adapter bolt circle 508 and distal hub bolt circle 538 of the respective mounting bolt clearance holes 500, 502, 504, 506 and mounting bolt threaded holes 530, 532, 534, 536. The distal end adapter 14 can then be rotated relative to the distal hub 316 to axially align the mounting bolt clearance holes 500, 502, 504, 506 with the mounting bolt threaded holes 530, 532, 534, 536.

It will be appreciated that the axial alignment of the bolt circles 508, 538 need not be limited to the distal end adapter 14 having the annular circular shape convex section or protuberance 540 and the distal hub 316 having the corresponding annular circular shape concave section or recess 542. The converse also is possible; that is, the distal hub 314 may include an annular circular shape convex section or protuberance that mates with a corresponding annular circular shape concave section or recess in the distal end adapter 14. Also, the annular protuberance 540 and annular recess 542 may be other than circular in shape, for example, a regular polygon shape or the like. It will further be appreciated that although in the illustrative embodiment the annular protuberance 540 and annular recess 542 are radially outward from the respective bolt circles 508, 538, in an alternate embodiment the annular protuberance 540 and annular recess 542 may be radially inward of the respective bolt circles 508, 538.

Referring to FIG. 14, once aligned, mounting bolts 548, more specifically shoulder bolts, may be inserted through the mounting bolt clearance holes 500, 502, 504, 506 and threaded into the mounting bolt threaded holes 530, 532, 534, 536 and tightened to an appropriate torque. The bearing support connection component 64 is then connected to the distal hub 316 of the load balancing arm 40 and may then be slidably receive and retain therein for rotatable movement the accessory spindle 340 of the accessory 88 88 by engaging the afore described retaining clip 358 in the groove 356.

In the illustrative embodiment, the distal end adapter 14 has mounting bolt clearance holes 500, 502, 504, 506 that are counterbored, and the distal hub 316 has mounting bolt threaded holes 530, 532, 534, 536. The invention is not so limited and other embodiments are contemplated. The mounting bolt clearance holes 500, 502, 504, 506 need not be counterbored; rather, the mounting bolt clearance holes 500, 502, 504, 506 may be straight bored and the head of the mounting bolts may instead engage a bottom surface of the interface 74 of the distal end adapter 14. In an embodiment, the distal end adapter 14 may have mounting bolt threaded holes, and the distal hub 316 may have mounting bolt clearance holes. To access mounting clearance holes in the distal hub 316, one or more cover plates 552 may be removed from the underlying structure of the distal hub 316. In another embodiment, the distal end adapter 14 may have a combination of mounting bolt clearance holes and mounting bolt threaded holes, and the distal hub 316 may have a combination of mounting bolt clearance holes and mounting bolt threaded holes. In still a further embodiment, both the distal end adapter 14 and the distal hub 316 have mounting bolt clearance holes, and threaded mounting bolts are passed through the holes and secured into place by means of a nut or the like.

The as-shown distal end adapter 14 has four mounting bolt holes 500, 502, 504, 506 and the as shown distal hub 316 similarly has four mounting bolt holes 530, 532, 534, 536. Other quantities are also envisaged although the distal end adapter 14 and distal hub 316 should have at least two mounting bolt holes for appropriate load distribution between the two components. Thus, two, three, five, or more, mounting bolt holes may be suitable. It will also be appreciated that the distal end adapter 14 may have fewer or a greater quantity of mounting bolt holes than the distal hub 316. For example, the distal end adapter 14 may have two mounting bolt holes and the distal hub 316 may have two, four, six or eight mounting bolt holes, or other multiples of two. The distal end adapter 14 may have three mounting bolt holes and the distal hub 316 may have three, six, or nine mounting bolt holes, or other multiples of three.

The four mounting bolt holes 500, 502, 504, 506 of the distal end adapter 14 are equally angularly spaced apart about the central axis B-B, as are the four mounting bolt holes 530, 532, 534, 536 of the distal hub 316 of the load balancing arm 40. Thus, the body 54 of the distal end adapter 14 may be connected to the distal hub 316 in at least four different angular positions of the body 54 about the central axis B-B. In this regard, the four mounting bolt holes 500, 502, 504, 506 may be aligned respectively with the four mounting bolt holes 530, 532, 534, 536 for a first angular position; or aligned respectively with the four mounting bolt holes 532, 534, 536, 530 for a second angular position that is 90 degrees away from the first angular position; or aligned respectively with the four mounting bolt holes 534, 536, 530, 532 for a third angular position that is 180 degrees away from the first angular position; or aligned respectively with the four mounting bolt holes 536, 530, 532, 534 for a fourth angular position that is 270 degrees away from the first angular position.

Other embodiments are also contemplated. Thus, the interface 74 of the distal end adapter 14 may have two or more mounting bolt holes (two, three, four, five, or more) equally angularly spaced apart about the central axis B-B such that the body 54 is connectable to the distal hub 316 of the load balancing arm 40 in at least two different angular positions of the body 54 about the central axis B-B. For two equally angularly spaced apart mounting bolt holes in the distal end adapter 14 and the distal hub 316, the body 54 of the distal end adapter 14 may be connected to the distal hub 316 in two different angular positions of the body 54 about the central axis B-B, where the second angular position is 180 degrees away from the first angular position. For three equally angularly spaced apart mounting bolt holes in the distal end adapter 14 and the distal hub 316, the body 54 of the distal end adapter 14 may be connected to the distal hub 316 in three different angular positions of the body 54 about the central axis B-B, where the second angular position is 120 degrees away from the first angular position, and the third angular position is 120 degrees away from the second angular position. For five holes, the angular spacing would be 72 degrees; for six holes, the angular spacing would be 60 degrees; and so on.

In the illustrative embodiment, the distal end adapter 14 and the distal hub 316 each have a single respective bolt circle 508, 538, and the bolt circles 508, 538 have the same diameter. As will be appreciated, the distal end adapter 14 and/or the distal hub 316 may have multiple bolt circles and some of the bolt circles may be on different diameters. For example, the distal end adapter 14 may have not only the mounting bolt holes 500, 502, 504, 506 on the adapter bolt circle 508 that are mateable with the mounting bolt holes 530, 532, 534, 536 on the distal hub 316, but also a different set of mounting bolt holes on a different adapter bolt circle that are mateable with mounting bolt holes on a different distal hub.

Referring to FIGS. 5 and 14, the distal end adapter 14 may include one or more rotational stops, one rotational stop 580 in the illustrative embodiment, that protrudes from a portion of the connection component 64 end of the body 54 and is radially offset from the central axis B-B. As shown in FIG. 5, the rotational stop 580 is angularly offset from the mounting bolt holes 500, 502, 504, 506. The rotational stop 580, as its name suggests, stops rotation of the accessory 88 relative to the distal hub 316 at the distal end 300 of the load balancing arm 40. As shown in FIG. 14, the accessory 88 includes a corresponding rotational stop 588 in its upper surface 590 that lies in the same plane perpendicular to the central axis B-B as the rotational stop 580 when the accessory spindle 340 is installed in the distal end adapter 14. As will be appreciated, the rotational stop 588 permits approximately a 340 degree range of rotational movement (assuming each rotational stop 580, 588 has a 10 degree angular footprint) of the accessory 88 relative to the distal end 300 of the load balancing arm 40 about the central axis B-B. Additional rotational stops can be employed in the distal end adapter 14 and/or the accessory upper surface 590 to limit the rotation of the accessory 88 relative to the load balancing arm 40 to any necessary or desired angular range.

In an embodiment, the one or more rotational stops 588 can be configured to be removable. Further, the distal end adapter 14 may have a plurality of mounting holes into which to insert the rotational stops 588. For continuous rotation applications, for example as may be the case for light head type accessories, the rotational stop 588 can be removed from the distal end adapter 14, or omitted from the construction of the distal end adapter 14.

Figure 17:
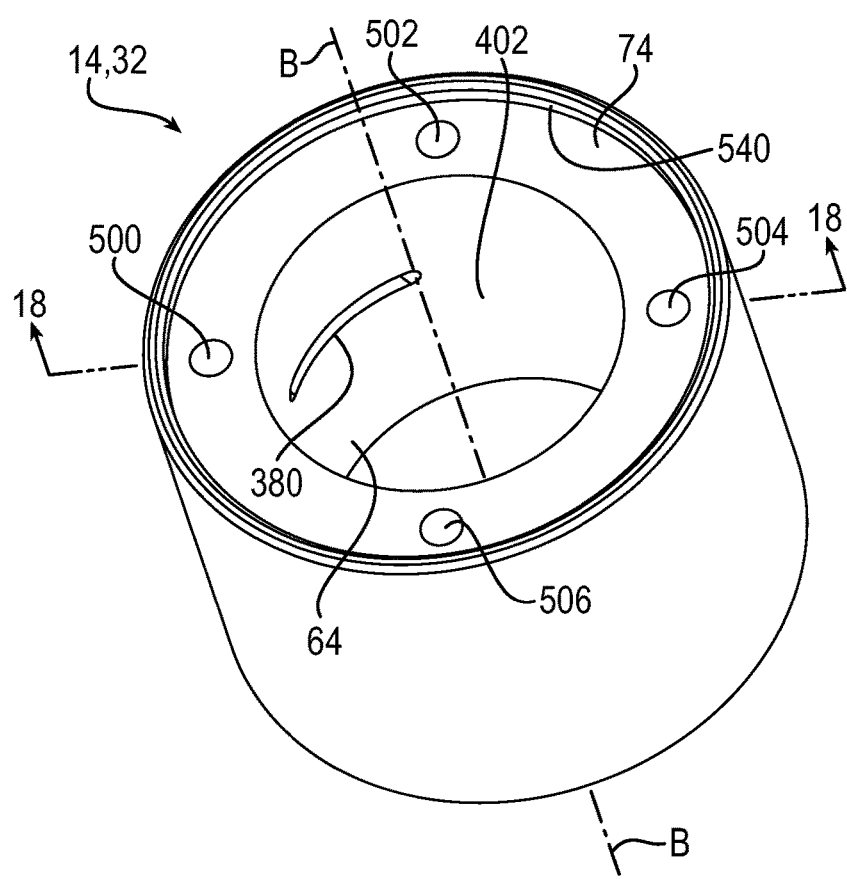
FIG. 17 is a top perspective view of a distal end adapter in accordance with another embodiment of the invention, showing a retaining clip guideway, bearing support and mounting bolt holes.
Figure 18:
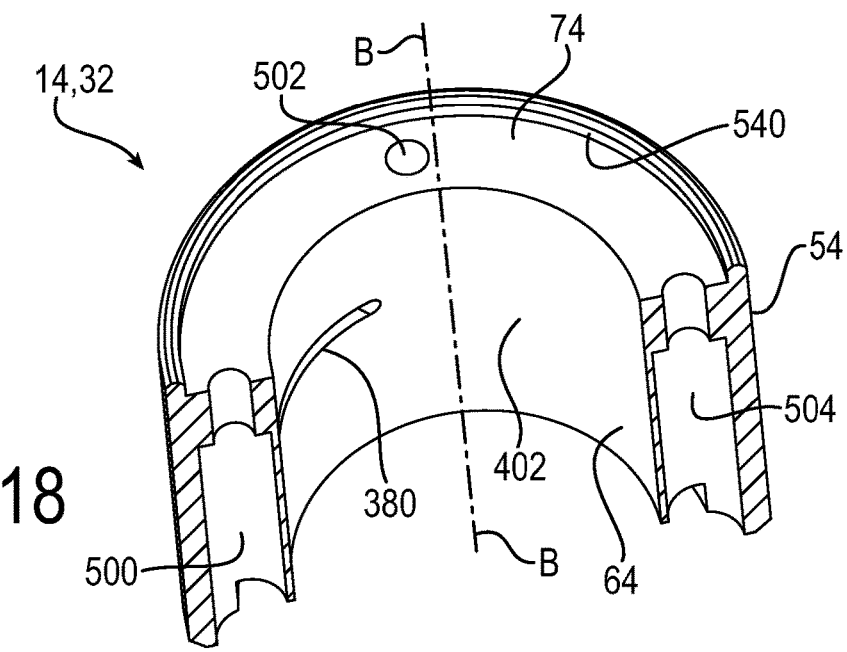
FIG. 18 is a cross section view of the FIG. 17 distal end adapter as viewed from the plane 18-18 in FIG. 17.

FIGS. 17 and 18 show a distal end adapter 14, 32 in accordance with another embodiment of the invention. The FIGS. 17-18 distal end adapter 14, 32 differs from the FIGS. 4, 5 and 15 distal end adapter 14, 30 in that the distal end adapter 14, 32 has a longer axial dimension, the cavity 402 has a larger diameter, and the guide slot 380 for the retaining clip 358 is inside the body 54 rather than at the interface 74 surface of the body 54. Thus, the distal end adapter 14, 32 is mateable to the distal hub 316 of the load balancing arm 40 in the same manner as described above with respect to the distal end adapter 14, 30. As will be appreciated, because the load balancing arm 40 can be mated with either of the two distal end adapters 30, 32, the load balancing arm 40 is not limited to a single dedicated connection interface at its distal end.

FIGS. 12 and 13 illustrate a load balancing arm 40 with some of the available options for the distal end adapters 30, 32, two in the illustrative embodiment, with FIG. 13 showing the distal end adapter 30 connected to the distal hub 316 of the load balancing arm 40. The distal end adapters 30, 32 shown can be said to represent a short bearing support adapter 30 and a long bearing support adapter 32. The two different length/diameter bearing support adapters 30, 32 enable the same load balancing arm 40 to be compatible with an accessory 88 having an accessory spindle 340 length and diameter such as shown in FIG. 14, or to be compatible with an accessory having an accessory spindle length and diameter relatively larger than that of the accessory spindle 340.

The distal end adapter 14 may be constructed to provide options other than different lengths and bearing support diameters. In an embodiment, three different distal end adapters 14 may have three different configurations of bearing support connection component 64. This would enable the load balancing arm 40 to be rotatably connectable to, for example, three different accessory spindles of three different accessories. Thus, for example, a first distal end adapter may have a first configuration bearing support connection component 64 that would be rotatably connectable to a first accessory having a first accessory spindle configuration; a second distal end adapter may have a second configuration bearing support connection component 64 that would be rotatably connectable to a second accessory having a second accessory spindle configuration; and, a third distal end adapter may have a third configuration bearing support connection component 64 that would be rotatably connectable to a third accessory having a third accessory spindle configuration. The same load balancing arm 40 would be mateable to three different accessory spindle configurations of three different accessories simply by the provision of three different distal end adapters 14. As will be appreciated, this avoids the need for the manufacture of three different load balancing arms having their own distal end bearing support connection interface integrally part of the load balancing arm structure.

Referring now to FIGS. 1, 8, 12, 13 and 16, in the illustrative embodiment the outer castings of the proximal hub 190 and the distal hub 316 are the same component; that is, the outer hub portions of the proximal hub 190 and the distal hub 316 have a one part geometry. Thus, the geometry and layout are the same for the respective interfaces 220, 318, the respective bolt circles 238, 538 and mounting holes 200, 202, 204, 206, 230, 232, 234, 236, the respective recesses 242, 542 and ledges 244, 544, and the respective cover panels 252, 552. The identical geometries eliminate the need for extra unique component designs and simplify assembly of the load balancing arm 40. It will be appreciated that the outer castings of the proximal hub 190 and distal hub 316 may have different geometries, or components or features thereof may have some identical geometries and some different geometries.

Although the invention has been shown and described with respect to a certain embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A medical device support system adapter for connection to a load balancing arm of a medical device support system, comprising:
    a body having a central axis;
    a connection component at one end of the body that is rotatably connectable about the central axis to another component of the medical device support system;
    an interface at an opposite end of the body that is connectable to a hub of the load balancing arm of the medical device support system;
    wherein the interface has at least two mounting bolt holes equally angularly spaced apart about the central axis such that the body is connectable to the hub of the load balancing arm in at least two different angular positions of the body about the central axis;
    further comprising an annular protuberance that is mateable with a corresponding annular protuberance of the hub to axially align the adapter with the hub;
    wherein the annular protuberance of the adapter projects axially from the interface either to form an annular convex section or an annular concave section that is mateable with the corresponding annular protuberance of the hub.

2. The medical device support system adapter of claim 1, wherein the connection component includes a drop tube that is rotatably connectable to a support structure of the medical device support system.

3. The medical device support system adapter of claim 1, wherein the connection component includes a bearing support that is rotatably connectable to an accessory of the medical device support system.

4. The medical device support system adapter of claim 1, wherein the at least two mounting bolt holes are on a bolt circle having the central axis as its center.

5. The medical device support system adapter of claim 1, wherein the at least two mounting bolt holes include mounting bolt clearance holes.

6. The medical device support system adapter of claim 5, wherein the mounting bolt clearance holes are counterbored.

7. The medical device support system adapter of claim 1, wherein the annular structures are circular shape.

8. The medical device support system adapter of claim 1, further comprising at least one rotational stop protruding from a portion of the one end and radially offset from the central axis.

9. The medical device support system adapter of claim 1, wherein the interface has four mounting bolt holes equally angularly spaced apart about the central axis 90 degrees apart such that the body is connectable to the hub of the load balancing arm in four different angular positions of the body about the central axis.

10. An adapter for a load balancing arm of a medical device support system, the adapter including:
    a body having a central axis;

a drop tube at one end of the body that is rotatably connectable to a support structure of the medical device support system;
at least one rotational stop protruding from a portion of the one end and radially offset from the central axis; and,
an interface at an opposite end of the body that is connectable to a hub of the load balancing arm;
wherein the drop tube includes a spindle with a circular groove to radially receive a retaining clip to axially support the drop tube.

11. The adapter of claim 10, wherein the interface has at least two mounting bolt holes equally angularly spaced apart about the central axis such that the body is connectable to the hub of the load balancing arm in at least two different angular positions of the body about the central axis.

12. The adapter of claim 11, wherein the at least two mounting bolt holes are on a bolt circle having the central axis as its center.

13. The adapter of claim 11, wherein the rotational stop is angularly offset from the at least two mounting bolt holes.

14. The adapter of claim 10, in combination with a support structure of a medical device support system, wherein the support structure includes a horizontal extension arm, and wherein the drop tube is rotatably connectable to a knuckle joint assembly of the horizontal extension arm.

15. An adapter for a load balancing arm of a medical device support system, the adapter including:
a body having a central axis;
a bearing support at one end of the body that is rotatably connectable to an accessory of the medical device support system;
at least one rotational stop protruding from a portion of the one end and radially offset from the central axis; and
an interface at an opposite end of the body that is connectable to a hub of the load balancing arm;
wherein the body includes a radial groove to radially receive a retaining clip to axially support the accessory.

16. The adapter of claim 15, wherein the interface has at least two mounting bolt holes equally angularly spaced apart about the central axis such that the body is connectable to the hub of the load balancing arm in at least two different angular positions of the body about the central axis.

17. The adapter of claim 16, wherein the at least two mounting bolt holes are on a bolt circle having the central axis as its center.

18. The adapter of claim 16, wherein the rotational stop is angularly offset from the at least two mounting bolt holes.

19. The adapter of claim 15, in combination with an accessory of a medical device support system, wherein the accessory includes an accessory spindle, and wherein the bearing support is rotatably connectable to the accessory spindle of the accessory.

20. An interchangeable load balancing arm assembly for a medical device support system, comprising:
a load balancing arm having at least one hub; and,
a plurality of interchangeable adapters that are attachable and detachable to the hub, wherein each of the plurality of interchangeable adapters includes a connection component having an associated connection component diameter and being rotatably connectable about an axis of rotation to another component of the medical device support system;
wherein the plurality of interchangeable adapters have different axial lengths and/or different associated connection component diameters;
wherein the load balancing arm includes a counterbalancing arm;
wherein the at least one hub includes a proximal hub and a distal hub at opposite ends of the counterbalancing arm, and the plurality of interchangeable adapters includes a plurality of interchangeable drop tube adapters that are attachable and detachable to the proximal hub and a plurality of interchangeable bearing support adapters that are attachable and detachable to the distal hub.

21. The interchangeable load balancing arm assembly of claim 20, wherein each of the plurality of adapters includes a body having a central axis, wherein the connection component is provided at one end of the body and an interface is provided at an opposite end of the body, the plurality of adapters being attachable and detachable to the hub of the load balancing arm via the interface.

22. The interchangeable load balancing arm assembly of claim 21, wherein the interface has at least two mounting bolt holes equally angularly spaced apart about the central axis such that the body is connectable to the hub of the load balancing arm in at least two different angular positions of the body about the central axis.

23. The interchangeable load balancing arm assembly of claim 20, wherein the plurality of interchangeable adapters includes respectively a plurality of interchangeable drop tube adapters, and each interchangeable drop tube adapter includes a drop tube that is rotatably connectable to a support structure of the medical device support system, and the drop tubes of the plurality of interchangeable drop tube adapters have different axial lengths and/or different associated drop tube diameters.

24. The interchangeable load balancing arm assembly of claim 20, wherein the plurality of interchangeable adapters includes respectively a plurality of interchangeable bearing support adapters, and each interchangeable bearing support adapter includes a bearing support that is rotatably connectable to an accessory of the medical device support system, and wherein the bearing supports of the plurality of interchangeable bearing support adapters have different axial lengths and/or different associated bearing support diameters.

25. The interchangeable load balancing arm assembly of claim 20, wherein the at least one hub includes a proximal hub and a distal hub, wherein the proximal hub includes a first outer hub portion and the distal hub includes a second outer hub portion, wherein the first and second outer hub portions have a one part geometry.

26. A medical device support system adapter for connection to a load balancing arm of a medical device support system, comprising:
a body having a central axis;
a connection component at one end of the body that is rotatably connectable about the central axis to another component of the medical device support system;
an interface at an opposite end of the body that is connectable to a hub of the load balancing arm of the medical device support system;
wherein the interface has at least two mounting bolt holes equally angularly spaced apart about the central axis such that the body is connectable to the hub of the load balancing arm in at least two different angular positions of the body about the central axis;
wherein the connection component includes a drop tube that is rotatably connectable to a support structure of the medical device support system;

wherein the drop tube includes a spindle with a circular groove to radially receive a retaining clip to axially support the drop tube.

27. A medical device support system adapter for connection to a load balancing arm of a medical device support system, comprising:
- a body having a central axis;
- a connection component at one end of the body that is rotatably connectable about the central axis to another component of the medical device support system;
- an interface at an opposite end of the body that is connectable to a hub of the load balancing arm of the medical device support system;
- wherein the interface has at least two mounting bolt holes equally angularly spaced apart about the central axis such that the body is connectable to the hub of the load balancing arm in at least two different angular positions of the body about the central axis;
- wherein the connection component includes a bearing support that is rotatably connectable to an accessory of the medical device support system;
- wherein the body includes a radial groove to radially receive a retaining clip to axially support the accessory.

* * * * *